(12) United States Patent
Matula, Jr. et al.

(10) Patent No.: US 9,339,625 B2
(45) Date of Patent: May 17, 2016

(54) OVER-MOLDED ROTATIONALLY COUPLED ASSEMBLIES

(75) Inventors: Jerome Matula, Jr., Apollo, PA (US); Anthony Vincent Startare, Belle Vernon, PA (US); Gregory John Jablonski, Butlet, PA (US); Derrick Blake Andrews, Markleton, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/008,685

(22) PCT Filed: Apr. 11, 2012

(86) PCT No.: PCT/IB2012/051752
§ 371 (c)(1),
(2), (4) Date: Sep. 30, 2013

(87) PCT Pub. No.: WO2012/143819
PCT Pub. Date: Oct. 26, 2012

(65) Prior Publication Data
US 2014/0183857 A1 Jul. 3, 2014

Related U.S. Application Data

(60) Provisional application No. 61/476,444, filed on Apr. 18, 2011.

(51) Int. Cl.
| | | |
|---|---|---|
| F16L 13/00 | (2006.01) |
| A61M 16/08 | (2006.01) |
| B29C 45/00 | (2006.01) |
| B29C 45/14 | (2006.01) |
| F16L 27/08 | (2006.01) |
| F16L 33/34 | (2006.01) |
| A61M 16/06 | (2006.01) |
| B29L 31/24 | (2006.01) |

(52) U.S. Cl.
CPC ....... *A61M 16/0875* (2013.01); *A61M 16/0816* (2013.01); *A61M 16/0825* (2014.02); *B29C 45/0017* (2013.01); *B29C 45/14598* (2013.01); *B29C 45/14614* (2013.01); *F16L 27/0804* (2013.01); *F16L 33/34* (2013.01); *A61M 16/0683* (2013.01); *B29L 2031/24* (2013.01)

(58) Field of Classification Search
USPC ................. 285/278, 275, 285.1, 286.1, 286.2
See application file for complete search history.

(56) References Cited

U.S. PATENT DOCUMENTS

| | | | |
|---|---|---|---|
| 3,000,049 | A | 9/1961 | Terry |
| 3,167,330 | A * | 1/1965 | Draudt ............................. 285/7 |
| 3,670,726 | A * | 6/1972 | Mahon et al. ................. 285/278 |
| 4,844,512 | A * | 7/1989 | Gahwiler ....................... 285/275 |
| 5,062,420 | A | 11/1991 | Levine |
| 5,837,180 | A * | 11/1998 | Linder et al. .................. 264/230 |
| 6,607,684 | B1 | 8/2003 | Lee |
| 7,487,772 | B2 | 2/2009 | Ging |

(Continued)

FOREIGN PATENT DOCUMENTS

| | | |
|---|---|---|
| DE | 2601345 A1 | 1/1976 |
| WO | WO9115981 A1 | 10/1991 |
| WO | WO2010023590 A2 | 3/2010 |

*Primary Examiner* — Aaron Dunwoody
(74) *Attorney, Agent, or Firm* — Michael W. Haas

(57) ABSTRACT

An assembly including a first component and a second component movably coupled to the first component. The second component is formed about and coupled to at least a portion of the first component via an over-molding process.

11 Claims, 6 Drawing Sheets

(56) References Cited

U.S. PATENT DOCUMENTS

| | | | |
|---|---|---|---|
| 7,862,366 B2* | 1/2011 | Stone et al. | 439/352 |
| 2005/0001425 A1* | 1/2005 | deCler et al. | 285/305 |
| 2007/0163600 A1 | 7/2007 | Hoffman | |
| 2007/0209663 A1 | 9/2007 | Marque | |
| 2009/0044808 A1 | 2/2009 | Guney | |
| 2009/0184514 A1* | 7/2009 | Williams | 285/226 |
| 2009/0230674 A1* | 9/2009 | Villaire et al. | 285/179 |
| 2010/0313891 A1 | 12/2010 | Veliss | |

* cited by examiner

OVER-MOLDED ROTATIONALLY COUPLED ASSEMBLIES

CROSS-REFERENCE TO RELATED APPLICATIONS

This patent application claims the priority benefit under 35 U.S.C. §371 of international patent application no. PCT/IB2012/051752, filed Apr. 11, 2012, which claims the priority benefit under 35 U.S.C. §119(e) of U.S. Provisional Application No. 61/476,444 filed on Apr. 18, 2011, the contents of which are herein incorporated by reference.

BACKGROUND OF THE INVENTION

1. Field of the Invention

The present invention pertains to over-molded rotationally coupled assemblies. More particularly, the invention relates to over-molded rotationally coupled assemblies for use in conduits for delivering a flow of gas to the airway of a patient.

2. Description of the Related Art

There are numerous situations where it is necessary or desirable to deliver a flow of breathing gas to the airway of a patient. For example, it is known to deliver a flow of breathing gas to a patient during at least a portion of the breathing cycle to treat breathing and/or cardiac disorders such as obstructive sleep apnea syndrome, chronic obstructive pulmonary disease, congestive heart failure, respiratory distress syndrome, and other breathing and/or cardiac disorders.

Generally, a pressure generating device is employed to produce the flow of breathing gas that is delivered to a patient interface device via a patient conduit. The patient interface device is structured to receive the flow of breathing gas from the patient conduit and deliver such flow to the airway of the patient.

The patient interface device may be, for example, a nasal mask, full-face mask (i.e., a nasal/oral mask), or a total face mask structured to be placed on and/or over the face of the patient. The patient interface device typically includes a mask cushion and shell. A headgear assembly, which typically contacts the back and/or top of the patient's head, may be employed to secure the patient interface device to the patient.

The patient conduit that supplies such patient interface devices generally includes one or more rotational couplings to allow freedom of movement and prevent binding of the conduit. Such rotational couplings are typically made using snap together components that require mating clearances between the two parts. A concern of the use of such components is that the mating clearances generally form vacant cavities that can harbor dirt or biological agents and thus are difficult to sanitize or sterilize. Another concern is that such "snap" components may become "unsnapped" and thus disengaged.

SUMMARY OF THE INVENTION

Accordingly, it is an object of one or more embodiments of the present invention to overcome the shortcomings of existing devices by providing rotationally coupled devices using an over-mold method. The invention allows for components to be joined in a sealed fashion, thereby eliminating clearance gaps required by other methods. Additionally, the components are coupled in a much more permanent manner than previously known snap connections.

In accordance with an aspect of the present invention, an assembly including a first component and a second component is provided. The second component is movably coupled to the first component. The second component is formed about and coupled to at least a portion of the first component via an over-molding process.

The first component may include a first tubular member having a first end and an opposite second end. The second component may include a second tubular member having a first end and an opposite second with the first end of the second tubular member being movably coupled via an over-molding process to the second end of the first component. One of the first end of the first component and the second end of the second component may be adapted to be coupled to a conduit carrying a pressurized flow of gas from a pressure generating device and the other one of the first end of the first component and the second end of the second component may be adapted to be coupled to a conduit coupled to a patient interface device. The second end of the first component may comprise an outward extending flange. The first tubular member and the second tubular member may define a sealed passage therethrough.

The first component may include a generally spherical portion, a cylindrical portion, and a cylindrical passage defined therein. The second component may include a generally planar face portion having an aperture disposed therein and an inner flange portion which generally extends from a periphery of the aperture and is shaped to define at least a portion of a generally spherical recess. The generally spherical portion of the first component may be movably coupled in the generally spherical recess. The cylindrical portion of the first component may be adapted to be coupled to a conduit coupled to a patient interface device. The generally planar face portion of the second component may be adapted to be coupled to, or integrally formed with, a housing portion of a pressure generating device.

The first component may include a first end and an opposite second end, the second end including a number of laterally protruding members. The second component may include a generally planar member having a number of housings protruding therefrom. Each housing of the number of housings may be disposed about, and movably coupled to, a respective one of the number of laterally protruding members.

In accordance with another aspect of the present invention, an assembly including a first component, a second component, and a coupling member is provided. The second component is movably coupled to the first component via the coupling member. The coupling member is formed about a portion of the first component and about a portion of the second component via an over-molding process.

The first component may include a first tubular member having a first end and an opposite second end. The second component may include a second tubular member having a first end and an opposite second end, wherein the first end of the second tubular member is movably coupled to the second end of the first tubular member by a coupling member formed via an over-molding process. One of the first end of the first component and the second end of the second component may be adapted to be coupled to a conduit carrying a pressurized flow of gas from a pressure generating device and the other one of the first end of the first component and the second end of the second component may be adapted to be coupled to a conduit coupled to a patient interface device. The second end of the first component may include an outward extending flange and the first end of the second component may include an outward extending flange, and the coupling member may generally encompasses the outward extending flange of the first component and the outward extending flange of the second component. The first tubular member and the second tubular member may define a sealed passage therethrough.

The second end of the first tubular member may be spaced a predetermined distance from the first end of the second tubular member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
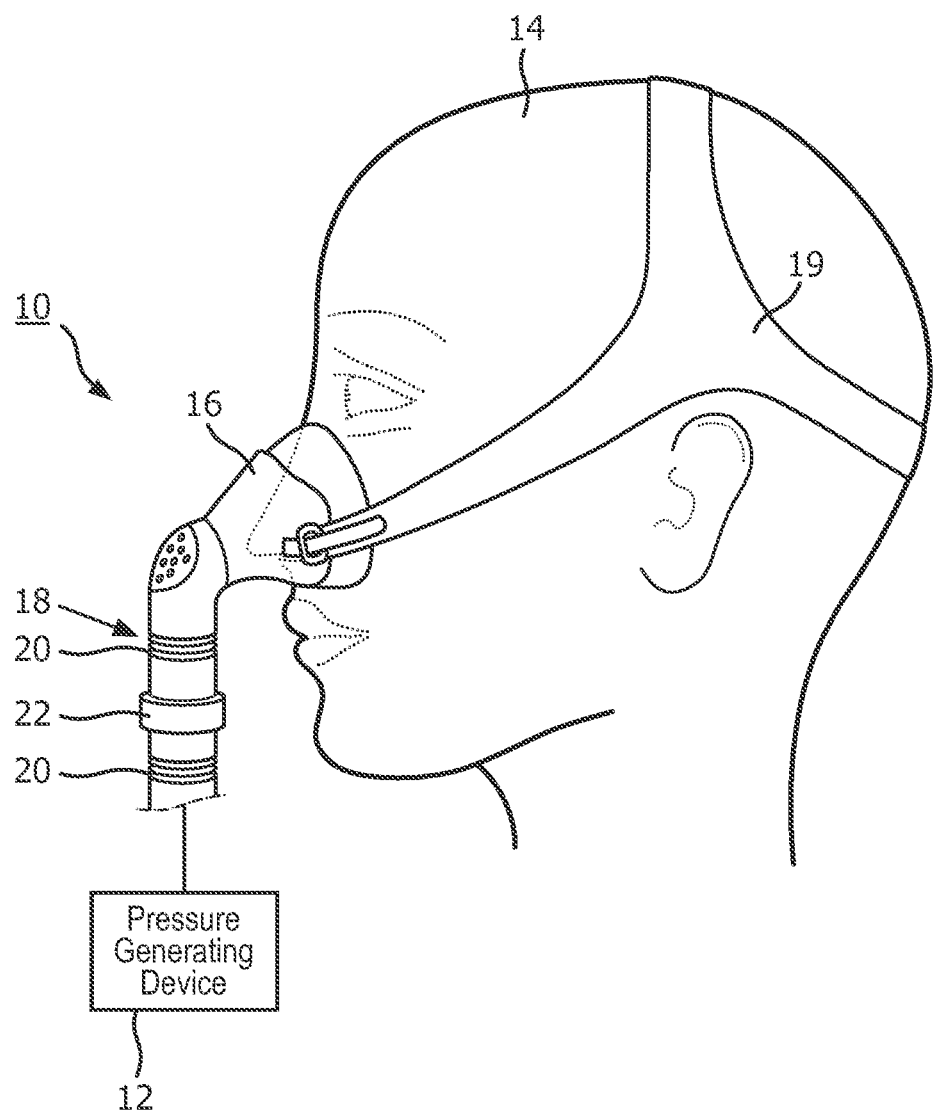
FIG. 1 is a schematic view of a system adapted to provide a regimen of respiratory therapy according to one embodiment of the present invention.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

An exemplary embodiment of a system 10 adapted to provide a regimen of respiratory therapy to a patient 14 according to the principles of the present invention is generally shown in FIG. 1. System 10 includes a pressure generating device 12, a patient circuit 18, and a patient interface device 16 coupled to the head of patient 14 by a headgear assembly 19. Pressure generating device 12 is structured to generate a flow of breathing gas and may include, without limitation, ventilators, pressure support devices (such as a continuous positive airway pressure device, or CPAP device), variable pressure devices (e.g., BiPAP®, Bi-Flex®, or C-Flex™ devices manufactured and distributed by Respironics, Inc. of Murrysville, Pa.), and auto-titration pressure support systems.

Patient circuit 18 is structured to communicate the flow of breathing gas from pressure generating device 12 to patient interface device 16 and includes one or more tubular conduit members 20 and rotational couplings 22. Patient circuit 18 may also be referred to as a patient conduit. Patient interface device 16 may be a nasal mask, a full-face mask, or a total face mask structured to be placed on and/or over a portion of the face of patient 14. Any type of patient interface device 16, however, which facilitates the non-invasive delivery of the flow of breathing gas communicated from pressure generating device 12 to the airway of patient 14 may be used while remaining within the scope of the present invention. Although discussed in conjunction with patient interface devices adapted for non-invasive delivery of the flow of breathing gas, it is contemplated that the present invention may be adapted for patient interface devices adapted for invasive delivery of the flow of breathing gas without varying from the scope of the present invention. As shown in FIG. 1, patient interface device 16 is directly coupled with patient conduit 18; other arrangements, however, are contemplated.

Figure 2:
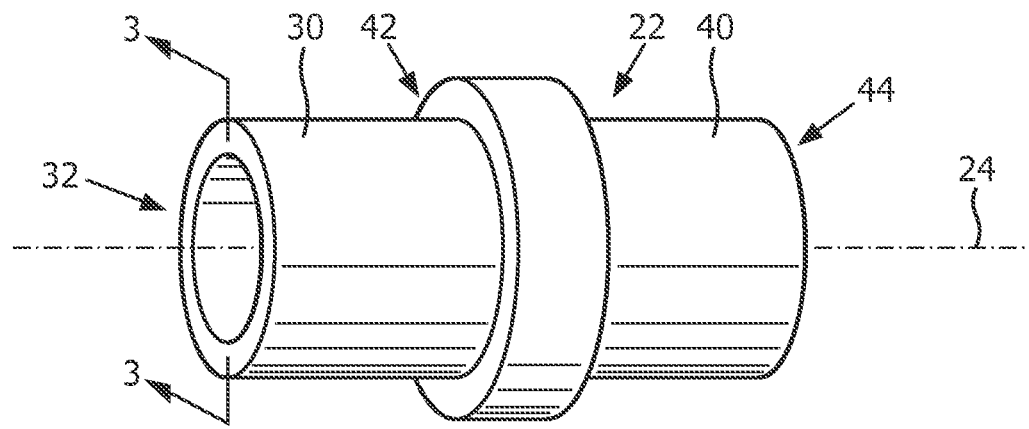
FIG. 2 shows an isometric view of a coupling assembly according to an exemplary embodiment of the present invention.
Figure 3:
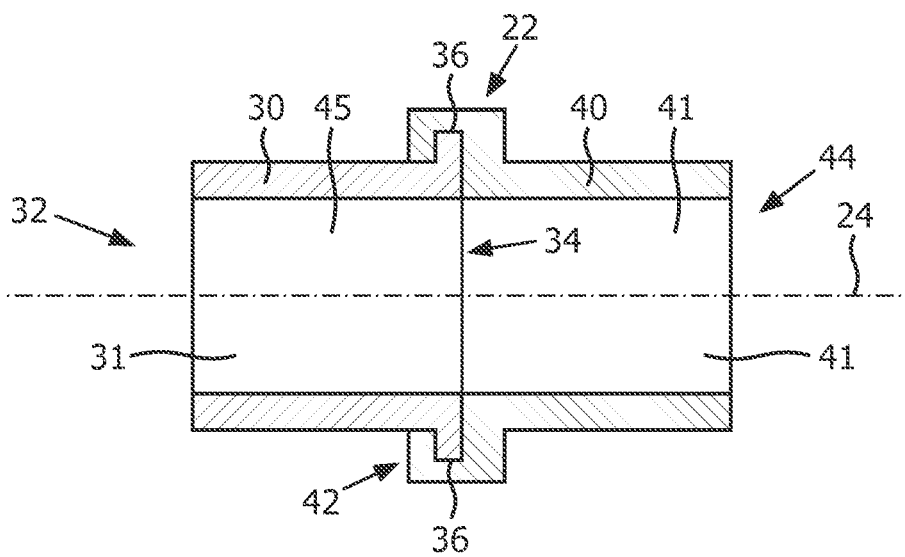
FIG. 3 shows a cross-sectional view of the coupling assembly of FIG. 2 along line 3-3.

FIGS. 2 and 3 illustrate side isometric and cross-sectional views, respectively, of a rotational coupling, or coupling assembly 22 according to an exemplary embodiment of the present invention. Assembly 22 includes a first component 30 and a second component 40 disposed generally about a central longitudinal axis 24. First component 30 is formed as a generally tubular member defining a passage 31 therein. First component 30 includes a first end 32 and an opposite second end 34. As shown in the cross-sectional view of FIG. 3, second end 34 includes a flange portion 36 which extends generally outward from longitudinal axis 24. Second component 40 is also formed as a generally tubular member defining a passage 41 therein. Second component 40 includes a first end 42 and an opposite second end 44. However, unlike first component 30, first end 42 of second component 44 is formed about second end 34 of first component 30 such that first end 42 of second component 40 is movably coupled to second end 34 of first component 30 such that either component 30, 40 may rotate with respect to the other component 30, 40 about longitudinal axis 24.

The coupling of first and second components 30 and 40 is accomplished by forming second component 40 in place with respect to a preformed first component 30 via an over-molding process. For example, coupling assembly 22 shown in FIGS. 2 and 3 may be formed by placing first component 30 on a cylindrical mold piece (not shown) having an outer diameter generally equal to the inner diameter (not numbered) of first component 30. First component 30 may be formed, for example, without limitation, from a polycarbonate or other suitable material preferably having a much higher melt temperature than the second component. A polycarbonate material may have a melt temperature of about 267 degrees Celsius. An outer mold section (or sections) that defines the shape of the outer periphery of second component 40 is then positioned about the cylindrical mold piece and the corresponding portion (second end 34) of first component 30. Next the desired material from which second portion 40 is to be formed is placed into the outer mold section via suitable means (e.g., without limitation, injection) and allowed to sufficiently harden. Second component 40 is preferably formed from a material having a lower melt temperature than the material of first component 30. For example, without limitation, polypropylene having a melt temperature of about 170 degrees Celsius has been found to be a suitable material.

It is to be readily appreciated that by using a material having a lower melting point, the over-molding of second component 40 does not compromise the geometry of first component 30. It is also to be readily appreciated that the distinct difference in chemical makeup of the two materials tends to eliminate any bonding between the two materials and thus reduces the likelihood of any binding or squeaking when used as moving components as described herein. A further benefit of using two dissimilar materials is the difference in shrink rate after molding. When used in an applications for the delivery of air, molding in different geometries where the two materials interface can add sealing elements that otherwise would not be possible to achieve.

After second component 40 has been suitably formed, the outer mold and cylindrical mold piece are removed thus generally leaving the coupling assembly 22 illustrated in FIGS. 2 and 3. It is to be appreciated that such example molding process is given for example purposes only and that other suitable over-molding processes may be employed without varying from the scope of the present invention.

By forming second component 40 directly onto first component 30 via an over-molding process, very little to no gap or space is created in the junction between the two components. Accordingly, such tight coupling of components 30 and 40 creates a single sealed passage 45 there through created by the coupling of passages 31 and 41. Additionally, as second component 40 is formed in place around a portion of first component 30, such coupling of components 30 and 40 is generally permanent. As shown in FIG. 1, coupling assembly 22 may be employed as a swivel mechanism in which first end 32 of first component 30 and second end 44 of second component 40 are each coupled to respective conduit members 20 of patient circuit 18.

Figure 4:
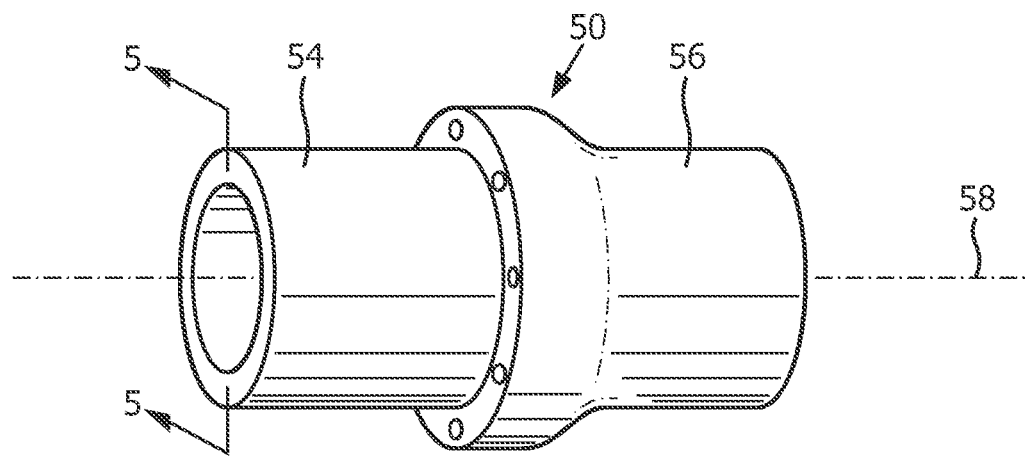
FIG. 4 shows an isometric view of a coupling assembly according to another exemplary embodiment of present invention.
Figure 5:
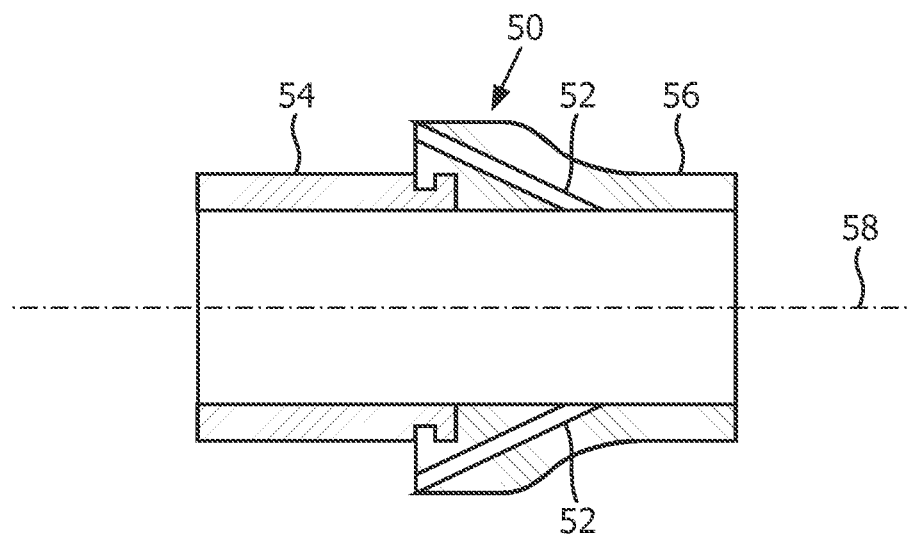
FIG. 5 shows a cross-sectional view of the coupling assembly of FIG. 4 along lone 5-5.

FIGS. 4 and 5 illustrate side isometric and cross-sectional views, respectively, of an exemplary swivel assembly 50 having internally molded exhalation channels 52 according to another exemplary embodiment of the present invention. Similar to the embodiment previously discussed in regard to FIGS. 2 and 3, swivel assembly 50 includes a first component 54 and a second component 56 that are movably coupled such that each component can rotate with respect to the other component about a central longitudinal axis 58. Also, like the embodiment previously discussed in regard to FIGS. 2 and 3, second component 54, as well as the internally molded exhalation channels 52 therein, are formed movably coupled to first component 52 via an over-molding process. Like coupling assembly 22 previously discussed, swivel assembly 50 may be coupled in patient circuit 18 through conventional coupling means.

Figure 6:
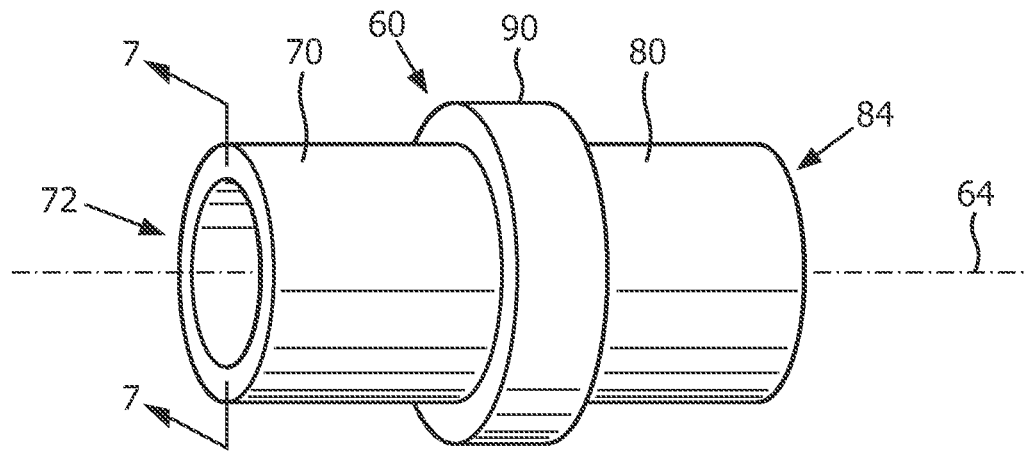
FIG. 6 shows an isometric view of a coupling assembly according to a further exemplary embodiment of the present invention.
Figure 7:
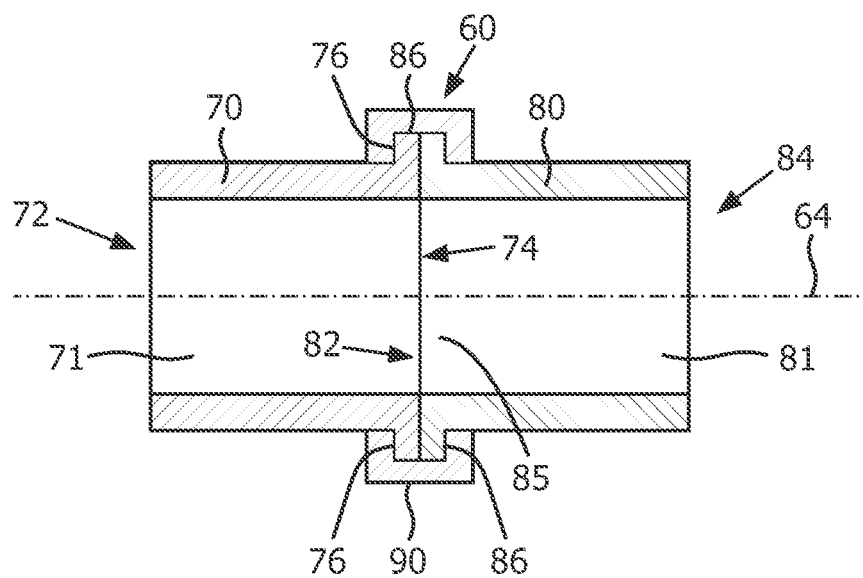
FIG. 7 shows a cross-sectional view of the coupling assembly of FIG. 6 along line 7-7.

FIGS. 6 and 7 illustrate side isometric and cross-sectional views, respectively, of another rotational coupling, or coupling assembly 60 according to an exemplary embodiment of the present invention. Assembly 60 includes a first component 70 and a second component 80 disposed generally about a central longitudinal axis 64. First component 70 is formed as a generally tubular member defining a passage 71 therein. First component 70 includes a first end 72 and an opposite second end 74. As shown in the cross-sectional view of FIG. 7, second end 74 includes a flange portion 76 which extends generally outward from longitudinal axis 64. Like first component 70, second component 80 is also formed as a generally tubular member defining a passage 81 therein and includes a first end 82 and an opposite second end 84. First end 82 includes a flange portion 86 which extends generally outward from longitudinal axis 64. Coupling assembly 60 further includes a coupling member 90 disposed about second end 74 of first component 70 and first end 82 of second component 80. Coupling member 90 couples first and second components 70 and 80 such that first end 82 of second component 80 is movably coupled to second end 74 of first component 70 such that either component 70, 80 may rotate with respect to the other component 70, 80 about longitudinal axis 64.

The coupling of first and second components 70 and 80 is accomplished by forming coupling member 90 in place with respect to preformed first and second components 70 and 80 via an over-molding process. For example, coupling assembly 60 may be formed by placing first component 70 and second component 80 on a cylindrical mold piece (not shown) having an outer diameter generally equal to the inner diameter (not numbered) of first and second components 70 and 80. An outer mold section (or sections) that defines the shape of the outer periphery of coupling member 90 is then positioned about the cylindrical mold piece and the corresponding portions (second end 74 and first end 82) of first and second components 70 and 80. Next the desired material from which coupling member 90 is to be formed is placed into the outer mold section via suitable means (e.g., without limitation, injection) and allowed to sufficiently harden. Finally the outer mold and cylindrical mold piece are removed thus generally leaving the coupling assembly 60 as illustrated in FIGS. 6 and 7. It is to be appreciated that such example molding process is given for example purposes only and that other suitable over-molding processes may be employed without varying from the scope of the present invention.

By forming coupling member 90 directly onto first and second components 70 and 80 via an over-molding process, very little to no gap or space is created in the junction between the two components. Accordingly, such tight coupling of components 70 and 80 creates a single sealed passage 85 there through created by the coupling of passages 71 and 81. Like coupling assemblies 22 and 50 previously discussed, swivel assembly 60 may be coupled in patient circuit 18 through conventional coupling means.

Figure 8:
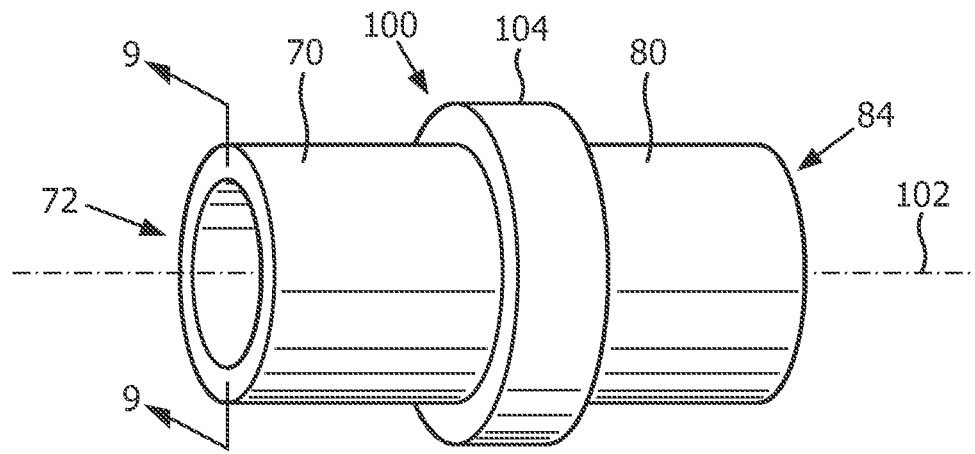
FIG. 8 shows an isometric view of a coupling assembly according to yet another exemplary embodiment of the present invention.
Figure 9:
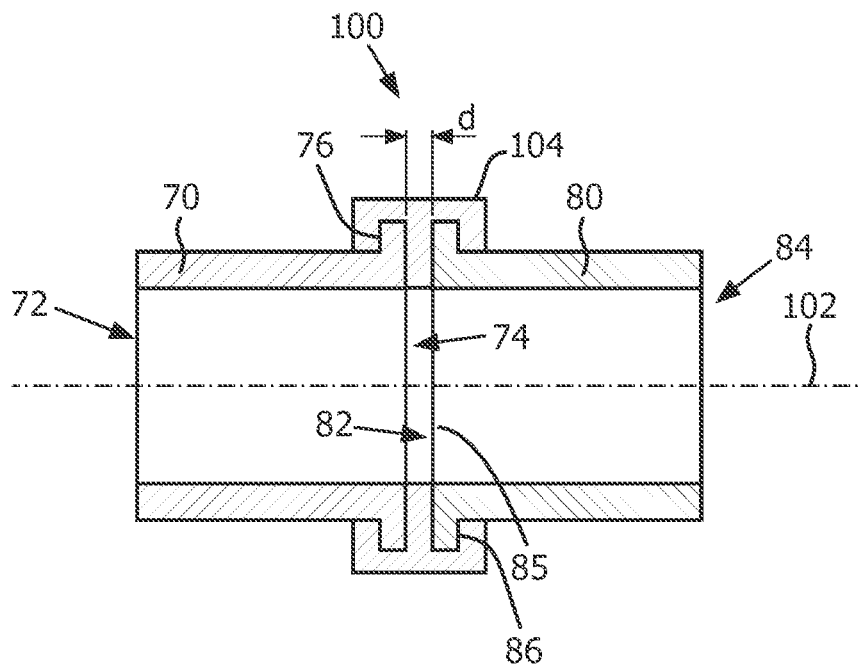
FIG. 9 shows a cross-sectional view of the coupling assembly of FIG. 8 along line 9-9.

FIGS. 8 and 9 illustrate side isometric and cross-sectional views, respectively, of a rotational coupling, or coupling assembly 100 according to another exemplary embodiment of the present invention. Assembly 100 is of similar construction as assembly 60 of FIGS. 6 and 7 except second end 74 of first component 70 and first end 82 of second component 80 are spaced apart a predetermined distance d along a central longitudinal axis 102. A coupling member 104, formed via an over-molding process, couples first and second components 70 and 80 together such that each of components 70, 80 may rotate with respect to the other component 70, 80 about longitudinal axis 102. As shown in the cross-sectional view of FIG. 9, coupling member 104 occupies the gap formed between components 70 and 80 thus providing a sealed rotatable coupling.

Figure 10:
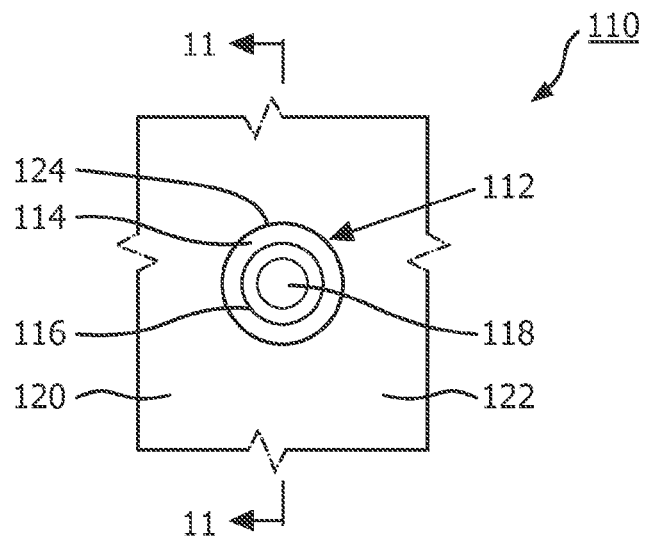
FIG. 10 shows an elevation view of a ball and socket assembly according to an exemplary embodiment of the present invention.
Figure 11:
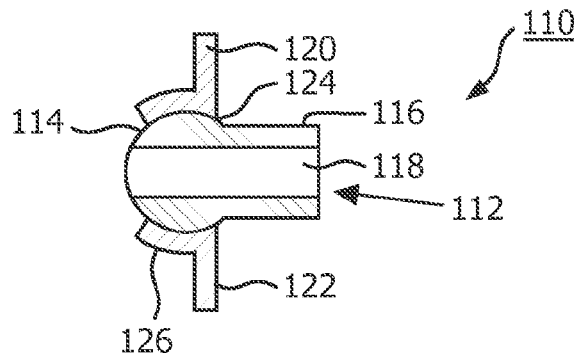
FIG. 11 shows a cross-sectional view of the ball and socket assembly of FIG. 10 along line 11-11.

FIGS. 10 and 11 illustrate front elevation and side cross-sectional views, respectively, of a coupling assembly 110 according to another exemplary embodiment of the present invention that may be employed, for example, without limitation, as a connection port on a pressure generating device (such as pressure generating device 12 of FIG. 1) for coupling a conduit (such as conduit 20 of FIG. 1). Unlike the assemblies previously discussed which provided examples of couplings rotatable only about a single axis, assembly 110 provides an example of a generally spherical coupling that is generally free to move about more than one axis. Assembly 110 includes a first component 112 having a generally spherical portion 114, a cylindrical portion 116, and a cylindrical passage 118 defined therethrough. Cylindrical portion 116 is adapted to have a conduit, such as conduit 20 of FIG. 1 coupled thereto through any suitable coupling means.

Continuing to refer to FIGS. 10 and 11, assembly 110 further includes a second component 120 having a generally planar face portion 122 having a aperture 124 disposed therein. Second component 120 further includes an inner flange portion 126 which generally extends from a periphery (not numbered) of aperture 124 and is shaped to define at least a portion of a generally spherical recess (not numbered) in which spherical portion 114 of first component 110 is movably coupled. When employed on a pressure generating device, such as pressure generating device 12 of FIG. 1, second component 120 would preferably either be coupled to, or formed as an integral portion of an outer housing of the pressure generating device.

Similar to the exemplary embodiments previously discussed, the coupling of first and second components 112 and 120 is accomplished by forming second component 120 in place with respect to a preformed first component 112 via an over-molding process. By forming second component 120 directly onto first component 112 via an over-molding process, very little to no gap or space is created in the junction between the two components, thus creating a sealed coupling. Additionally, as previously discussed, such coupling of components 112 and 120 is generally permanent.

Figure 12:
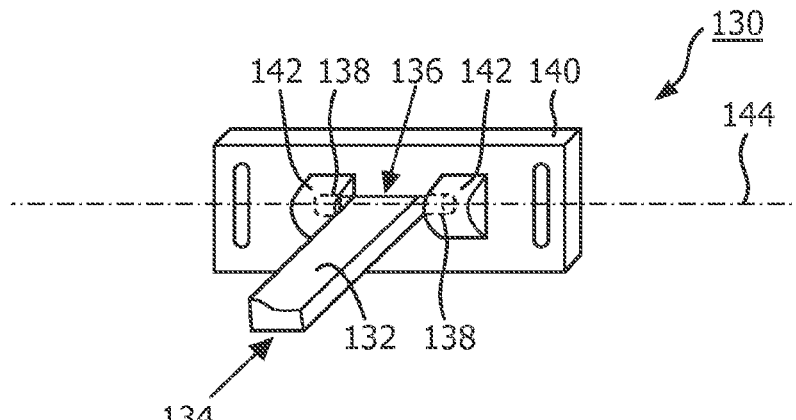
FIG. 12 shows an isometric view of yet another assembly according to an exemplary embodiment of the present invention.

FIG. 12 illustrates an assembly 130, formed according to an exemplary embodiment of the present invention, that may be employed, for example, without limitation, as a forehead support of a patient interface device. Assembly 130 includes a first component 132 having a first end 134 and an opposite second end 136. First end 134 is adapted to be coupled to a portion of a patient interface device. Second end 136 includes a number (two in the illustrated example) of laterally protruding members 138.

Assembly 130 further includes a second component 140 of generally planar shape including a number (two in the illustrated example) of housings 142 that are each disposed to engage, and movably couple a respective one of the laterally protruding members 138 of first component 132. Such arrangement allows for first and second components 132 and 140 to move with respect to each other generally about an axis 144. When utilized as a forehead support, second component 140 would preferably include a forehead pad (not shown) disposed on the opposite side of housings 142.

Similar to the exemplary embodiments previously discussed, the coupling of first and second components 132 and 140 is accomplished by forming second component 140 in place with respect to a preformed first component 132 via an over-molding process. By forming second component 132 directly about each of laterally protruding members 138 via an over-molding process, first and second components 132 and 140 are movably coupled in a generally permanent manner.

Although the invention has been described in detail for the purpose of illustration based on what is currently considered to be the most practical and preferred embodiments, it is to be understood that such detail is solely for that purpose and that the invention is not limited to the disclosed exemplary embodiments, but, on the contrary, is intended to cover modifications and equivalent arrangements that are within the spirit and scope of the appended claims. Any example materials provided herein from which components may be formed are provided solely for example purposes and are not intended to be limiting upon the scope of the invention.

What is claimed is:

1. An assembly comprising:
    a first tubular member, of generally cylindrical shape, disposed about a central longitudinal axis and having a first end and an opposite second end, the second end including an outward extending flange; and
    a second tubular member, of generally cylindrical shape, disposed about the central longitudinal axis and having a first end and an opposite second end,
    wherein the first end of the second tubular member is formed about and generally permanently coupled to the outward extending flange of the first tubular member via an over-molding process, and
    wherein the first tubular member is readily rotatable with respect to the second tubular member around the central longitudinal axis.

2. The assembly according to claim 1, wherein one of the first end of the first tubular member and the second end of the second tubular member is adapted to be coupled to a conduit carrying a pressurized flow of gas from a pressure generating device and the other one of the first end of the first tubular member and the second end of the second tubular member is adapted to be coupled to a conduit coupled to a patient interface device.

3. The assembly according to claim 1, wherein the first tubular member and the second tubular member define a sealed passage therethrough.

4. An assembly comprising:
    a first tubular member having a first end and an opposite second end, the opposite second end having an outward extending flange; and
    a second tubular member having a first end and an opposite second end, the first end having a second outward extending flange,
    wherein the first tubular member and the second tubular member are rotatably coupled in a generally permanent manner via a coupling member formed about the outward extending flange of the first tubular member and the second outward extending flange of the second tubular member via an over-molding process.

5. The assembly according to claim 4, wherein one of the first end of the first tubular member and the second end of the second tubular member is adapted to be coupled to a conduit carrying a pressurized flow of gas from a pressure generating device and the other one of the first end of the first tubular member and the second end of the second tubular member is adapted to be coupled to a conduit coupled to a patient interface device.

6. The assembly according to claim 5, wherein the first tubular member and the second tubular member define a sealed passage therethrough.

7. The assembly according to claim 5, wherein the second end of the first tubular member is spaced a predetermined distance from the first end of the second tubular member.

8. The assembly according to claim 4, wherein the coupling member includes a recess of complimentary shape to the outward extending flange of the first tubular member and the second outward extending flange of the second tubular member.

9. The assembly according to claim 4, wherein:
the first tubular member is disposed about a longitudinal axis;
the outward extending flange comprises:
- a first surface facing along the longitudinal axis in a first direction,
- a second surface facing along the longitudinal axis in a second direction opposite the first direction, and
- a third surface disposed between the first surface and the second surface and facing away from the central longitudinal axis; and the coupling member includes a recess comprising a first surface and a second surface which each are disposed about and engage a corresponding one of the first and third surfaces of the outward extending flange.

10. An assembly comprising:
a first tubular member having a first end and an opposite second end, the second end including an outward extending flange; and
a second tubular member having a first end and an opposite second end, wherein the first end of the second tubular member includes a recess correspondingly shaped to the outward extending flange, wherein the recess is formed about and coupled to the outward extending flange of the first tubular member via an over-molding process,
wherein the first tubular member is readily moveable with respect to the second tubular member.

11. The assembly according to claim 10, wherein:
the first tubular member is disposed about a longitudinal axis;
the outward extending flange comprises:
- a first surface facing along the longitudinal axis in a first direction,
- a second surface facing along the longitudinal axis in a second direction opposite the first direction, and
- a third surface disposed between the first surface and the second surface and facing away from the central longitudinal axis; and the recess includes a first surface, a second surface, and a third surface which each are disposed about and engage a corresponding one of the first, second, and third surfaces of the outward extending flange.

\* \* \* \* \*